United States Patent
Takeuchi et al.

(10) Patent No.: US 10,442,744 B2
(45) Date of Patent: Oct. 15, 2019

(54) METHOD OF PRODUCING HYDROCHLOROFLUOROOLEFIN AND METHOD OF PRODUCING 2,3,3,3-TETRAFLUOROPROPENE

(71) Applicant: AGC Inc., Chiyoda-ku (JP)

(72) Inventors: Yu Takeuchi, Chiyoda-ku (JP); Hidekazu Okamoto, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/856,999

(22) Filed: Dec. 28, 2017

(65) Prior Publication Data

US 2018/0134639 A1     May 17, 2018

Related U.S. Application Data

(63) Continuation of application No. PCT/JP2016/069464, filed on Jun. 30, 2016.

(30) Foreign Application Priority Data

Jun. 30, 2015 (JP) .................................. 2015-130833

(51) Int. Cl.

| C07C 17/358 | (2006.01) |
|---|---|
| B01J 23/06 | (2006.01) |
| B01J 23/26 | (2006.01) |
| B01J 27/122 | (2006.01) |
| B01J 27/125 | (2006.01) |
| B01J 27/128 | (2006.01) |
| C07C 17/23 | (2006.01) |
| C07C 21/18 | (2006.01) |
| B01J 21/04 | (2006.01) |
| B01J 23/44 | (2006.01) |
| B01J 37/08 | (2006.01) |
| B01J 21/06 | (2006.01) |
| C07B 61/00 | (2006.01) |

(52) U.S. Cl.
CPC ............ *C07C 17/358* (2013.01); *B01J 21/04* (2013.01); *B01J 23/06* (2013.01); *B01J 23/26* (2013.01); *B01J 23/44* (2013.01); *B01J 27/122* (2013.01); *B01J 27/125* (2013.01); *B01J 27/128* (2013.01); *B01J 37/08* (2013.01); *C07C 17/23* (2013.01); *C07C 21/18* (2013.01); *B01J 21/06* (2013.01); *C07B 61/00* (2013.01)

(58) Field of Classification Search
CPC ....... C07C 17/358; C07C 21/18; C07C 17/23; B01J 23/26; B01J 27/12; B01J 37/26
See application file for complete search history.

(56) References Cited

U.S. PATENT DOCUMENTS

| 2010/0152504 A1 | 6/2010 | Hulse et al. |
|---|---|---|
| 2010/0163781 A1 | 7/2010 | Sharratt et al. |
| 2010/0197980 A1 | 8/2010 | Nappa |
| 2010/0204529 A1 | 8/2010 | Terada et al. |
| 2011/0218370 A1 | 9/2011 | Elsheikh et al. |
| 2011/0319680 A1 | 12/2011 | Kawaguchi et al. |
| 2012/0215037 A1 | 8/2012 | Sun et al. |
| 2013/0079562 A1 | 3/2013 | Sharratt et al. |
| 2014/0171698 A1 | 6/2014 | Elsheikh et al. |
| 2014/0228600 A1 | 8/2014 | Elsheikh et al. |
| 2015/0191405 A1 | 7/2015 | Nishiguchi et al. |

FOREIGN PATENT DOCUMENTS

| JP | 2010-523635 | 7/2010 |
|---|---|---|
| JP | 2010-529111 | 8/2010 |
| JP | 2010-536777 | 12/2010 |
| JP | 2012-509324 | 4/2012 |
| JP | 2012-512160 | 5/2012 |
| JP | 2013-180964 | 9/2013 |
| JP | 2014-513673 | 6/2014 |
| WO | WO 2008/125825 A2 | 10/2008 |
| WO | WO 2009/026082 A1 | 2/2009 |
| WO | WO 2009/035130 A2 | 3/2009 |
| WO | WO 2010/059496 A1 | 5/2010 |
| WO | WO 2010/068715 A2 | 6/2010 |
| WO | WO 2011/162338 A1 | 12/2011 |
| WO | WO 2012/115930 A1 | 8/2012 |
| WO | WO 2014/046251 A1 | 3/2014 |

OTHER PUBLICATIONS

Nomura et al (JP 2013180964 A machine translation), Sep. 2013.*
International Search Report dated Sep. 13, 2016 in PCT/JP2016/069464, filed on Jun. 30, 2016 (with English Translation).
Written Opinion dated Sep. 13, 2016 in PCT/JP2016/069464, filed on Jun. 30, 2016.

* cited by examiner

*Primary Examiner* — Jafar F Parsa
(74) *Attorney, Agent, or Firm* — Oblon, McClelland, Maier & Neustadt, L.L.P.

(57) ABSTRACT

There is provided an industrially advantageous and efficient method of producing a Z-isomer of HCFO-1224yd or HCFO-1223xd by isomerizing an E-isomer thereof. The method produces HCFO (Z-isomer) by causing specific HCFO (E-isomer) contained in a raw material composition to undergo an isomerization reaction under a condition where the HCFO (E-isomer) is isomerized.

15 Claims, No Drawings

METHOD OF PRODUCING HYDROCHLOROFLUOROOLEFIN AND METHOD OF PRODUCING 2,3,3,3-TETRAFLUOROPROPENE

CROSS-REFERENCE TO RELATED APPLICATIONS

This application is a continuation of prior International Application No. PCT/JP2016/069464, filed on Jun. 30, 2016 which is based upon and claims the benefit of priority from Japanese Patent Application No. 2015-130833, filed on Jun. 30, 2015; the entire contents of all of which are incorporated herein by reference.

FIELD

The present invention relates to a method of producing hydrochlorofluoroolefin and a method of producing 2,3,3,3-tetrafluoropropene.

BACKGROUND (Z)-1-chloro-2-3,3,3-tetrafluoropropene (HCFO-1224yd (Z)) and (Z)-1,2-dichloro-3,3,3-trifluoropropene (HCFO-1223xd (Z)) are useful as raw materials of, for example, a foaming agent of hard polyurethane foam, a solvent, a cleaning agent, a refrigerant, a working fluid, a propellant, and fluorocarbon resin.

In this specification, an abbreviation of a compound being halogenated hydrocarbon is given in a parenthesis after the name of the compound, and the abbreviation is used instead of the name of the compound as required. Further, as for a compound having a double bond in its molecule and existing as an E-isomer and a Z-isomer, its E-isomer and Z-isomer are respectively represented by (E) and (Z) each added at the end of the abbreviation of the compound. An abbreviation of a compound name without the notation of (E) or (Z) at the end represents an E-isomer and/or a Z-isomer.

As a method of producing HCFO-1224yd, US 2012/0215037 A1 describes a method to obtain HCFO-1224yd by bringing vapor-phase 1,2-dichloro-2-3-3-3-tetrafluoropropane (HCFC-234ba) into contact with a potassium chloride catalyst carried by carbon to cause the HCFC-234ba to undergo a dehydrochlorination reaction. Further, WO 2009/035130 A1 describes a method to obtain HCFO-1224yd by causing 1-chloro-2,2,3,3,3-pentafluoropropane (HCFC-235cb) to undergo a dehydrofluorination reaction by using a base such as potassium hydroxide. WO 2009/035130 A1 also describes to obtain 2,3,3,3-tetrafluoropropene (HFO-1234yf) by hydrogen-reducing the obtained HCFO-1224yd in the presence of a catalyst.

Further, WO 2011/162338 A1 describes a method to obtain HFO-1234yf by causing a raw material compound gas containing at least one of 1,1-dichloro-2,3,3,3-tetrafluoropropene (CFO-1214ya) and HCFO-1224yf to react with hydrogen in the presence of a palladium catalyst carried by carbon. WO 2011/162338 A1 also describes that as a result of the hydrogen reduction of CFO-1214ya, HCFO-1224yd is produced.

In these methods, however, HCFO-1224yd is usually obtained as a mixture of an E-isomer and a Z-isomer, which is inconvenient for the use of only one of the geometric isomers. This has given rise to a demand for a method to selectively produce one of HCFO-1224yd (E) and HCFO-1224yd (Z) by an industrially advantageous and efficient method.

There is also a demand for an industrially advantageous and efficient method that selectively produces one of an E-isomer and a Z-isomer of HCFO-1223xd similarly to the above.

SUMMARY

The present invention was made to solve the aforesaid problems and has an object to provide an industrially advantageous and efficient method that produces a Z-isomer of HCFO-1224yd or HCFO-1223xd by isomerizing an E-isomer thereof. It is another object of the present invention to provide a method of producing HFO-1234yf, the method capable of efficiently producing HFO-1234yf while inhibiting the production of by-products.

A method of producing hydrochlorofluoroolefin of the present invention includes: preparing a raw material composition containing a compound expressed by the following formula (1); and isomerizing the compound expressed by the following formula (1) under a condition where the compound expressed by the following formula (1) is isomerized, to produce a compound expressed by the following formula (2),

[Chem. 1]

formula(1)

[Chem. 2]

formula(2)

where X represents a fluorine atom or a chlorine atom.

A method of producing 2,3,3,3-tetrafluoropropene of the present invention includes: obtaining (Z)-1-chloro-2,3,3,3-tetrafluoropropene by the above-described method of producing hydrochlorofluoroolefin; and obtaining 2,3,3,3-tetrafluoropropene by hydrogen-reducing the (Z)-1-chloro-2,3,3,3-tetrafluoropropene obtained in the above step.

According to the method of producing HCFO of the present invention, it is possible to produce a Z-isomer of HCFO-1224yd or HCFO-1223xd by isomerizing an E-isomer thereof, by an industrially advantageous and efficient method. Further, according to the method of producing HFO-1234yf of the present invention, it is possible to efficiently produce HFO-1234yf while inhibiting the production of by-products.

DETAILED DESCRIPTION

Embodiments of the present invention will be hereinafter described in detail.

(Method of Producing HCFO)
A method of producing hydrochlorofluoroolefin (HCFO) of the present invention causes a compound expressed by the following formula (1) (hereinafter referred to as "HCFO (1)") contained in a raw material composition containing the HCFO (1) (hereinafter, also referred to as the raw material composition) to undergo an isomerization reaction under a condition where the compound expressed by the following formula (1) is isomerized, to produce a compound expressed by the following formula (2) (hereinafter referred to as "HCFO (2)"), as expressed by the following formula (3). HCFO (1) is an E-isomer of the HCFO, and HCFO (2) is a Z-isomer thereof.

[Chem. 3]

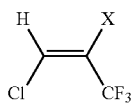

formula(1)

[Chem. 4]

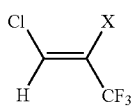

formula(2)

[Chem. 5]

formula(3)

In the above formula (1) and formula (2), X is a fluorine atom or a chlorine atom, and X in the above formula (1) and X in formula (2) are identical.

X that HCFO (1) used as a starting substance in the isomerization reaction expressed by the above formula (3) (hereinafter, simply referred to also as the "isomerization reaction") has is a fluorine (F) atom or a chlorine (Cl) atom. HCFO (1) that has the F atom as X is HCFO-1224yd (E), and HCFO (1) that has the Cl atom as X is HCFO-1223xd (E). These HCFO-1224yd (E) and HCFO-1223xd (E) both can be produced by well-known methods.

The raw material composition may be composed only of HCFO (1), or may be composed of HCFO (1) and a compound other than HCFO (1). Examples of the compound that the raw material composition contains other than HCFO (1) include HCFO (2) which is a Z-isomer of HCFO (1). Besides, the compound other than HCFO (1) may be a raw material for producing HCFO (1) and impurities such as by-products which are produced in addition to HCFO (1) when HCFO (1) is produced. Incidentally, in the case where the isomerization reaction is caused using the raw material composition containing the impurities, the by-products produced from the impurities can be removed by a known means such as distillation.

As for a method of producing HCFO (1) used as the starting material, specifically, HCFO-1224yd (E) that is HCFO (1) whose X is the F atom can be produced by a method of supplying a mixed gas of CFO-1214ya and hydrogen to a catalyst layer of palladium or the like carried on activated carbon to hydrogen-reduce CFO-1214ya. CFO-1214ya used in this method can be produced by a well-known method.

In the above method, HCFO-1224yd is usually obtained as a mixture of a Z-isomer and an E-isomer. In the method of producing HCFO of the present invention, the mixture of the Z-isomer and the E-isomer of HCFO-1224yd may be used as it is as the raw material composition as described above, or the Z-isomer and the E-isomer may be blended at a desired mixture ratio after separated by a well-known method such as distillation, to be used as the raw material composition. Further, HCFO-1224yd (E) may undergo the isomerization reaction as a raw material composition containing, in addition to HCFO-1224yd (E), impurities such as: CFO-1214ya which is the production raw material; by-products in a production step, such as 1-chloro-1,2,2,3,3,3-hexafluoropropane (HCFC-226ca), 1-chloro-1,1,2,2,3,3-hexafluoropropane (HCFC-226cb), 1-chloro-2,2,3,3,3-tetrafluoropropene (HCFO-1224xe), 1,1,1,2,2-pentafluoropropane (HFC-254eb), (E)-1,3,3,3-tetrafluoropropene (HFO-1234ze (E)), (Z)-1,3,3,3-tetrafluoropropene (HFO-1234ze (Z)), 1,1-dichloro-2,3,3,3-tetrafluoropropene (CFO-1214ya), 1,3-dichloro-1,2,3,3-tetrafluoropropene (CFO-1214yb), 1,2-dichloro-1,3,3,3-tetrafluoropropene (CFO-1214xb), 1-chloro-2,3,3,3-tetrafluoropropane (HCFC-244eb), 2,2-dichloro-1,1,3,3,3-pentafluoropropane (HCFC-225aa), 1,2-dichloro-1,2,3,3,3-pentafluoropropane (HCFC-225ba), 1,2-dichloro-1,1,2,3,3-pentafluoropropane (HCFC-225bb), 1,1-dichloro-2,2,3,3,3-pentafluoropropane (HCFC-225ca), 1,3-dichloro-1,1,2,2,3-pentafluoropropane (HCFC-225cb), 1,1-dichloro-1,2,2,3,3-pentafluoropropane (HCFC-225cc), HCFO-1223xd (E), HCFO-1223xd (Z); and HCFO-1224yd (Z) which is a target substance.

HCFO-1223xd (E) that is HCFO (1) whose X is the Cl atom can be obtained by, for example, a method of causing 1,1,2-trichloro-3,3,3-trifluoropropane (HCFC-233da) to react with a base such as potassium hydroxide in the presence of a phase-transfer catalyst.

In the above method, HCFO-1223xd is usually obtained as a mixture of a Z-isomer and an E-isomer. In the method of producing HCFO of the present invention, the mixture of the Z-isomer and the E-isomer of HCFO-1223xd may be used as it is as the raw material composition, or the Z-isomer and the E-isomer may be blended at a desired mixture ratio after separated by a well-known method such as distillation, to be used as the raw material composition. Further, HCFO-1223xd (E) may undergo the isomerization reaction as the raw material composition containing, in addition to HCFO-1223xd (E), impurities such as: HCFC-233da or the like which is a production raw material; by-products in a production step, such as 1-chloro-3,3,3-trifluoropropyne, (E)-1-chloro-3,3,3-trifluoropropene (HCFO-1233zd (E)), (Z)-1-chloro-3,3,3-trifluoropropene (HCFO-1233zd (Z)), and 1,1-dichloro-3,3,3-trifluoropropene (HCFO-1223za); HCFO-1223xd (Z) being a target substance; HCFO-1224yd (Z); and HCFO-1224yd (E).

(Condition of Isomerization)

Here, under the condition where the HCFO (1) undergoes the isomerization reaction to HCFO (2) as expressed by the aforesaid formula (3), an isomerization reaction of HCFO (2) to HCFO (1) usually progresses in parallel. That is, the isomerization reaction to/from HCFO (1) from/to HCFO (2) is an equilibrium reaction. The method of producing HCFO of the present invention causes the isomerization reaction under the condition where HCFO (1) is isomerized to HCFO (2) (hereinafter, also referred to as the "isomerization condition (1)") in the equilibrium reaction of the isomerization.

In an equilibrium state of the isomerization, HCFO (1) and HCFO (2) are present at a predetermined ratio. The present inventors have confirmed that the equilibrium ratio of HCFO (1) (E-isomer) and HCFO (2) (Z-isomer) in the equilibrium state of the isomerization under 150° C. and an atmospheric pressure is not less than 1.5/98.5 nor more than 4/96 in terms of a molar ratio expressed by HCFO (1)/HCFO (2).

The method of producing HCFO of the present invention efficiently produces HCFO (2) by quickly isomerizing HCFO (1) to HCFO (2) by subjecting HCFO (1) to the isomerization condition (1) and thereby increasing a reaction rate of the aforesaid isomerization reaction.

In the case where the raw material composition containing HCFO (1) and HCFO (2) is used in the equilibrium reaction of the isomerization, when a ratio of HCFO (1) and HCFO (2) in the raw material composition (hereinafter the "ratio of HCFO (1) and HCFO (2)" will be referred to as "HCFO (1)/HCFO (2)") is larger than HCFO (1)/HCFO (2) in the equilibrium state of the isomerization (hereinafter, HCFO (1)/HCFO (2) in the equilibrium state of the isomerization will be referred to as the "equilibrium ratio"), the isomerization condition (1) is satisfied and accordingly it is possible to isomerize HCFO (1) to convert it to HCFO (2).

Further, it is possible to improve a conversion rate from HCFO (1) to HCFO (2) within a range of, for example, the aforesaid preferable equilibrium ratio, by adjusting HCFO (1)/HCFO (2) in the raw material composition. From a viewpoint of improving the conversion rate from HCFO (1) to HCFO (2), HCFO (1)/HCFO (2) in the raw material composition is preferably 5/95 or more, and more preferably 30/70 or more in a molar ratio. Still more preferably, only HCFO (1) out of HCFO (1) and HCFO (2) is used as the raw material composition.

Incidentally, when HCFO (1)/HCFO (2) in the raw material composition is small, the apparent conversion rate from HCFO (1) to HCFO (2) is smaller than when HCFO (1)/HCFO (2) is large, but for example, as will be described later, by repeating the aforesaid isomerization reaction, the distillation separation of HCFO (1) and HCFO (2) which are obtained as a result of the isomerization reaction, and the re-isomerization of HCFO (1) obtained as a result of the distillation separation, it is possible to obtain HCFO (2) from HCFO (1) by an industrially advantageous and efficient method.

Further, by adjusting the isomerization condition to cause a reverse reaction of the isomerization reaction expressed by the aforesaid formula (3), it is also possible to convert HCFO (2) to HCFO (1). In this case, the isomerization reaction is caused under a condition where HCFO (2) is isomerized to HCFO (1) (hereinafter, also referred to as the "isomerization condition (2)").

An example of the isomerization condition (2) is a case where HCFO (1)/HCFO (2) in the raw material composition used in the equilibrium reaction of the isomerization is smaller than the equilibrium ratio in the equilibrium state of the isomerization. From a viewpoint of improving a conversion rate from HCFO (2) to HCFO (1), HCFO (1)/HCFO (2) in the raw material composition is preferably less than 5/95, and more preferably less than 1.5/98.5 in a molar ratio. Still more preferably, only HCFO (2) is used as the raw material composition. In the case where HCFO (1) is obtained through the isomerization reaction of HCFO (2) as well, by repeating the isomerization reaction from HCFO (2) to HCFO (1), the distillation separation of HCFO (1) and HCFO (2) which are obtained as a result of the isomerization reaction, and the re-isomerization of HCFO (2) obtained as a result of the distillation separation, it is possible to obtain HCFO (1) from HCFO (2) by an industrially advantageous and efficient method, similarly to the above.

Specific usable examples of a method to form the equilibrium of the aforesaid isomerization include a method of bringing HCFO (1) into contact with a metal catalyst in a reactor, a method of bringing HCFO (1) into contact with a radical generator in the reactor, and a method of heating HCFO (1). These methods can quickly form the equilibrium of the isomerization, and thus are suitable as an industrial method of producing HCFO (2) by isomerizing HCFO (1).

(Reactor)

The reactor in which HCFO (1) undergoes the isomerization reaction is not limited as long as it can endure later-described temperature and pressure in the reactor, and may be a cylindrical vertical reactor, for instance. As a material of the reactor, glass, iron, nickel, an alloy mainly composed of iron or nickel, or the like is used. Further, the reactor may include an electric heater or the like which heats the inside of the reactor.

(Isomerization Reaction)

The isomerization reaction expressed by the aforesaid formula (3) can be caused by either a batch-type method or a continuous flow-type method. The method of producing HCFO of the present invention is preferably the continuous method in view of production efficiency.

The raw material composition containing HCFO (1) is usually in a vapor phase in the isomerization reaction in the method of producing HCFO of the present invention. The raw material composition is preferably pre-heated before introduced into the reactor. A pre-heating temperature of the raw material composition at this time is preferably not lower than 20° C. nor higher than 300° C., and more preferably not lower than 50° C. nor higher than 250° C. from a viewpoint of vaporizing the raw material composition and improving reactivity. Hereinafter, the method of producing HCFO of the present invention will be described regarding a reaction condition in the case where the isomerization reaction of the raw material composition in the vapor phase is caused by the continuous method, but this is not restrictive.

In the case where the raw material composition is in the vapor phase in the isomerization reaction, a diluent gas is preferably supplied to the reactor together with the raw material composition from a viewpoint of the inhibition of a side reaction, the easy supply of the starting substance to the reactor, the adjustment of a flow rate, and the like. Further, in the case where the isomerization reaction expressed by the aforesaid formula (3) is caused in the presence of the later-described metal catalyst, the use of the diluent gas is advantageous in improving durability of the metal catalyst.

Examples of the diluent gas include nitrogen, a carbon dioxide gas, a rare gas (helium or the like), and an organic compound that is inert in the aforesaid isomerization reaction. Examples of the inert organic compound include saturated hydrocarbons such as methane, ethane, propane, butane, pentane, and hexane, and fluorohydrocarbons such as trifluoromethane ($CHF_3$, HFC-23), difluoromethane ($CH_2F_2$, HFC-32), pentafluoroethane ($CF_3$—$CHF_2$, HFC-125), tetrafluoroethane ($CF_3$—$CFH_2$, HFC-134a), trifluoroethane ($CF_3$—$CH_3$, HFC-143a), difluoroethane ($CF_2H$—$CH_3$, HFC-152a), and tetrafluoropropane ($CF_3$—$CFH$—$CH_3$, HFC-254eb). An amount of the diluent gas is not limited, but specifically, the amount is preferably not less than 1 mol % nor more than 10000 mol %, more preferably not less than 10 mol % nor more than 1000 mol %, and still more preferably not less than 30 mol % nor more than 500 mol % to HCFO (1) supplied to the reactor.

The raw material composition and the diluent gas are preferably pre-heated to the aforesaid preferable temperature before introduced to the reactor from a viewpoint of improving reactivity. The raw material composition and the diluent gas may be mixed after separately pre-heated to the aforesaid temperature, to be thereafter supplied to the reactor, or they may be pre-heated to the aforesaid temperature after mixed, to be thereafter supplied to the reactor.

(Isomerization by Contact with Metal Catalyst)

In the case where HCFO (1) is caused to undergo the isomerization reaction by being brought into contact with the metal catalyst, it is possible to cause the isomerization reaction by bringing HCFO (1) into contact with the metal catalyst in the reactor. Specifically, for example, the metal catalyst is put in the reactor to form a reaction part, and HCFO (1) is made to flow to the reaction part to undergo the isomerization reaction. In this case, the metal catalyst may be put either in a fixed bed type or in a fluidized bed type. In the case of the fixed bed type, it may be either a horizontal fixed bed type or a vertical fixed bed type, but the vertical fixed bed type is preferable because, when a mixed gas composed of a plurality of components is generated by the isomerization reaction, the vertical fixed bed type can easily prevent the concentration distribution of the components from varying depending on places due to their specific gravity difference.

The metal catalyst used in the isomerization reaction expressed by the aforesaid formula (3) has a catalytic action on the isomerization reaction expressed by the aforesaid formula (3). The metal catalyst is, for example, at least one kind of substance selected from a group consisting of a metal simple substance, a metal oxide, and a metal halide. As the metal catalyst, one kind of substance may be used alone, or a combination of two kinds of substances or more may be used.

Among these, the metal oxide or the metal halide is preferable as the metal catalyst since they each enables the efficient isomerization of HCFO (1) to HCFO (2).

An example of metal constituting the metal catalyst is at least one kind of element selected from a group consisting of a transition metal element, a group 12 metal element, and a group 13 metal element in the periodic table. Among these, the metal constituting the metal catalyst is preferably at least one kind of element selected from a group consisting of a group 4 metal element, a group 6 metal element, a group 8 metal element, a group 9 metal element, a group 10 metal element, a group 11 metal element, a group 12 metal element, and a group 13 metal element in the periodic table, and is more preferably at least one kind of element selected from a group consisting of a group 4 metal element, a group 6 metal element, a group 8 metal element, a group 10 metal element, a group 11 metal element, a group 12 metal element, and a group 13 metal element.

The metal constituting the metal catalyst is preferably titanium, zirconium, hafnium, chromium, iron, ruthenium, cobalt, rhodium, nickel, palladium, platinum, copper, zinc, or aluminum, and more preferably zirconium, chromium, iron, nickel, palladium, copper, zinc, or aluminum. In the case where the metal catalyst is a metal simple substance, the metal simple substance may be one kind of metal or may be an alloy of two kinds of metals or more, selected from the aforesaid metals. In the case where the metal catalyst is a metal oxide, the metal oxide may be an oxide of one kind or a composite oxide of two kinds or more, selected from the aforesaid metals. In the case where the metal catalyst is a metal halide, the metal halide may be a halide of one kind or a composite halide of two kinds or more, selected from the aforesaid metals.

Specific examples of the metal catalyst include iron, cobalt, nickel, palladium, chromium oxide (chromia), aluminum oxide (alumina), zinc oxide, iron fluoride, aluminum fluoride, aluminum chloride, chromium fluoride, and chromium chloride. Among these metal catalysts, one of substance or more selected from a group consisting of aluminum oxide (alumina) and chromium oxide (chromia) are preferable because they are easily available and enables the efficient isomerization of HCFO (1) to HCFO (2).

Further, the metal catalyst may be carried by a carrier. Examples of the carrier include an alumina carrier, a zirconia carrier, a silica carrier, a silica-alumina carrier, a carbon carrier represented by activated carbon, a barium sulfate carrier, and a calcium carbonate carrier. Examples of the activated carbon include activated carbons prepared from raw materials such as wood, charcoal, fruit shell, palm shell, peat, lignite, and coal.

Further, the metal catalyst is preferably subjected to activation treatment in advance in view of improving reactivity. An example of a method of the activation treatment is a method of bringing the metal catalyst into contact with an activator in the presence of heating or in the absence of heating. As the activator, hydrogen fluoride, hydrogen chloride, or fluorine-containing hydrocarbon is usable, for instance. As the activator, one kind may be used alone or two kinds or more may be used in combination. Among all, as the activator, fluorine-containing hydrocarbon is preferably used. As the fluorine-containing hydrocarbon used as the activator, trichlorofluoromethane (CFC-11), dichlorodifluoromethane (CFC-12), chlorotrifluoromethane (CFC-13), dichlorofluoromethane (HCFC-21), chlorodifluoromethane (HCFC-22), trifluoromethane (HFC-23), tetrafluoroethylene (FO-1114), or the like is suitable, for instance. HCFO-1224yd (E) or HCFO-1224yd (Z) being the raw material is also usable as the activator.

Further, the metal catalyst may be subjected to re-activation treatment in addition to the activation treatment applied before the reaction. That is, in the isomerization reaction, when the activity of the metal catalyst lowers and the conversion rate to HCFO (2) being the target substance lowers (when the formation of the equilibrium of the isomerization becomes difficult), the metal catalyst is preferably subjected to the re-activation treatment. Consequently, it is possible to regenerate the activity of the metal catalyst to reuse the metal catalyst. An example of a method of the re-activation treatment is a method of bringing the metal catalyst into contact with a treatment agent for the re-activation treatment (re-activator) in the presence of heating or in the absence of heating, as is done in the activation treatment before it is used. As the re-activator, oxygen, hydrogen fluoride, hydrogen chloride, chlorine-containing or fluorine-containing hydrocarbon, or the like is usable. Examples of the chlorine-containing or fluorine-containing hydrocarbon include carbon tetrachloride, chloroform, dichloromethane (HCC-30), chloromethane, vinyl chloride, CFC-11, CFC-12, CFC-13, CFC-21, HCFC-22, HFC-23, FO-1114, and HCFO-1224yd (E/Z). Further, in the re-activation treatment, an inert gas such as nitrogen, argon, or helium is usable for diluting the re-activator in view of the inhibition of a side reaction, a durability improvement of the metal catalyst, and so on.

The metal catalyst may be subjected to the activation treatment before put in the reactor, but the metal catalyst is preferably subjected to the activation treatment while put in the reactor because this facilitates the operation and is high in work efficiency. Accordingly, the activator is preferably introduced to the reactor in which the metal catalyst is put, to apply the activation treatment to the metal catalyst. The activator may be introduced to the reactor while kept at room temperature, but in view of improving reactivity, its temperature is preferably adjusted by heating or the like when introduced to the reactor.

Further, in order to enhance the efficiency of the activation treatment, the activation treatment is preferably performed in a state where the inside of the reactor is heated. In this case, the inside of the reactor is preferably heated to a temperature of not lower than 50° C. nor higher than 400° C.

HCFO (1) introduced into the reactor is thus brought into contact with the metal catalyst in the reactor. As for a reaction pressure at this time, in a case where, for example, the pressurization is required for the purpose of, for example, reducing the reaction time, a pressure condition can be 1.0 MPa or less, or in terms of an internal pressure in the reactor, the pressure condition can be not lower than a normal pressure nor higher than 1.0 MPa, but the reaction is preferably performed at a normal pressure or at a minute pressure of 0.2 MPa or lower, in view of easy industrial execution.

A contact temperature of HCFO (1) and the metal catalyst (reaction temperature) is not lower than 0° C. nor higher than 500° C., preferably not lower than 50° C. nor higher than 500° C., more preferably not lower than 50° C. not higher than 350° C., still more preferably not lower than 100° C. not higher than 250° C., and most preferably not lower than 150° C. nor higher than 250° C., in terms of the temperature in the reactor. Too low a reaction temperature makes it difficult to form the aforesaid equilibrium of the isomerization, leading to a decrease in the conversion rate of HCFO (1) to HCFO (2). On the other hand, too high a reaction temperature causes the production of by-products due to, for example, the decomposition of HCFO (1), leading to a decrease in the conversion rate to HCFO (2). Further, a contact time of HCFO (1) with the metal catalyst (reaction time) in the reactor is preferably not less than 0.1 seconds nor more than 1000 seconds, and more preferably not less than 1 second nor more than 100 seconds. Note that the contact time corresponds to a residence time of HCFO (1) in the reactor, and can be adjusted by adjusting a supply amount (flow rate) of HCFO (1) to the reactor.

(Isomerization by Contact with Radical Generator)

An example of a method to bring HCFO (1) into contact with the radical generator is a method of bringing HCFO (1) into contact with the radical generator activated by heat or light, in the reactor.

Examples of a method to bring HCFO (1) into contact with the activated radical generator in the reactor include a method of supplying the radical generator after the radical generator is activated in advance and a method of introducing a mixture of the radical generator and HCFO (1) to the reactor and activating the radical generator in the reactor. In both of the methods, either one of HCFO (1) and the radical generator may be supplied to the reactor first or they may be supplied simultaneously. That is, even in a case where at the time of the supply of one of HCFO (1) and the radical generator, the other has not been supplied to the reactor, it suffices that, while HCFO (1) or the radical generator supplied first resides, the component to be supplied later is supplied, the radical generator is appropriately activated, and finally HCFO (1) and the activated radical generator are in contact with each other in the reactor for a predetermined time. However, in order to efficiently bring the HCFO (1) into contact with the activated radical generator, it is preferable to supply the mixture in which HCFO (1) and the radical generator are mixed to the reactor and activate the radical activator in the reactor.

Further, the radical generator may be activated by either heat or light, or may be activated using the both, but industrially, it is preferably activated only by heat, and a method of supplying the mixture of HCFO (1) and the radical generator to the heated reactor and applying heat energy to the mixture in the reactor to activate the radical generator by heat is simple and thus is preferable.

The radical generator is activated by heat or light to generate a radical. The radical is a chemical species such as an atom, molecule, or ion with an unpaired electron, and its examples include a radical cation whose charge of the chemical species is positive, a radical anion whose charge of the chemical species is negative, a neutrally-charged radical, biradical, and carbene. Specific examples of the radical include a fluorine radical, a chlorine radical, a bromine radical, an iodine radical, an oxygen radical, a hydrogen radical, a hydroxy radical, a nitroxy radical, a nitrogen radical, an alkyl radical, a difluorocarbene, and a carbon radical.

The radical generator which generates the aforesaid radical is not limited as long as it generates the radical by being given external energy such as heat or light. Specifically, as the radical generator, one that easily generates the radical in a reaction system is preferable, and examples thereof include a halogen gas or halogenated hydrocarbon of chlorine, bromine, or the like, air, oxygen, ozone, and hydrogen peroxide. The halogenated hydrocarbon is halogenated hydrocarbon containing atoms of fluorine, chlorine, bromine, or iodine replacing part or all of hydrogen atoms bonded to carbon atoms in alkane such as methane, ethane, propane, butane, pentane, or hexene or in alkene such as ethene, propene, butene, pentene, or hexene, and the halogenated hydrocarbon contains at least one fluorine, chlorine, bromine, or iodine atom. Note that, as the halogenated hydrocarbon serving as the radical generator, the compounds which are the starting substance or the target substance in the method of producing HCFO of the present invention are not included, that is, HCFO-1224yd and HCFO-1223xd are not included. Further, a compound containing four or more fluorine atoms may have a difficulty in causing radical cleavage, and in this case, a radical generation condition such as temperature is preferably optimized as required. As the radical generator, one kind may be used alone or two kinds or more may be used in combination.

Specific examples of the halogenated hydrocarbon include $CH_3Cl$, $CH_2Cl_2$, $CHCl_3$, $CCl_4$, $CH_3CH_2Cl$, $CH_3CCl_3$, $CH_2ClCH_2Cl$, $CH_2=CCl_2$, $CHCl=CCl_2$, $CCl_2=CCl_2$, $CHCl_2CHCl_2$, $CCl_3CH_2Cl$, $CH_3CH_2CH_2Cl$, $CH_3CHClCH_3$, $CH_3CHClCH_2Cl$, $CH_3Br$, $CH_2Br_2$, $CHBr_3$, $CBr_4$, $CH_3CH_2Br$, $CH_3CBr_3$, $CH_2BrCH_2Br$, $CH_2=CBr_2$, $CHBr=CBr_2$, $CBr_2=CBr_2$, $CHBr_2CHBr_2$, $CBr_3CH_2Br$, $CH_3CH_2CH_2Br$, $CH_3CHBrCH_3$, $CH_3CHBrCH_2Br$, $CH_3I$, $CH_2I_2$, $CHI_3$, $CH_3CH_2I$, $CH_3CI_3$, $CH_2ICH_2I$, $CH_2=CI_2$, $CHI=CI_2$, $CI_2=CI_2$, $CHI_2CHI_2$, $CI_3CH_2I$, $CH_3CH_2CH_2I$, $CH_3CHICH_3$, $CH_3CHICH_2I$, $CF_2HCl$, $CF_3I$, $CF_2I_2$, $CF_3Br$, and $CF_2Br_2$.

As the radical generator, oxygen, air, and chlorine are preferable out of the above listed ones because of their low price and easy availability. Chlorine is suitable as the radical generator because of its easiness in generating the radical, but is very corrosive. Moreover, the use of chlorine as the radical generator necessitates washing a product produced after the isomerization reaction is finished, with an aqueous basic solution to which a reducing agent is added, and removing the chlorine. Further, the use of halogen or halogenated hydrocarbon as the radical generator may cause the generation of a minute amount of halides, that is, halides of HCFO (1) and HCFO (2) as by-products, making the refining of the target substance (HCFO (2)) difficult.

On the other hand, air and oxygen are advantageous because of their easiness in separating from by-products. Accordingly, air or oxygen is more preferably used as the radical generator.

An amount of the radical generator supplied to the reactor is preferably minute. This is because the generation of the radical occurs in chain. Excessively adding the radical generator leads to not only a waste of subsidiary materials but also a load in the step of separating the target substance or the starting substance from the radical generator after the reaction. Even in the use of oxygen or air which easily separates from the target substance and the starting substance, too large an addition amount of, for example, the air leads to a decrease in capability in an aggregation step and a distillation step. Further, excessively adding chlorine as the radical generator results in the production of the compound in which chlorine is added to a double bond of HCFO (1) and HCFO (2) (chlorine adduct) as described above. This chlorine adduct is hydrochlorofluorocarbon (HCFC) which is a global warming and ozone-depleting substance, and accordingly an amount of the by-produced chlorine adduct is preferably small.

In view of the above-described points, as for amounts of HCFO (1) and the radical generator, their molar ratio expressed by radical generator/HCFO (1) is preferably not less than 0.0001/99.9999 nor more than 10/90, and more preferably not less than 0.0001/99.9999 nor more than 0.1/99.95. Further, in a case where the radical generator is supplied as gas in this embodiment where HCFO (1) undergoes the reaction in the vapor phase, as for the amounts of the HCFO (1) and the radical generator, their volume ratio expressed by radical generator/HCFO (1) may be within the same range as the above molar ratio. In this embodiment where the aforesaid isomerization reaction is performed by the continuous method, supply amounts of HCFO (1) and the radical generator are expressed by supply amounts per unit time.

In the case where the radical generator is activated by heat in the aforesaid isomerization reaction, a reaction pressure at the time of the reaction is preferably a normal pressure or a minute pressure of 0.2 MPa or less as in the case where the catalyst is used. Further, too low a reaction temperature leads to the insufficient activation of the radical generator, leading to a decrease in the conversion rate of HCFO (1) to HCFO (2). On the other hand, too high a reaction temperature causes the production of by-products due to, for example, the decomposition of HCFO (1), leading to a decrease in the conversion rate to HCFO (2). Accordingly, the reaction temperature (contact temperature of HCFO (1) and the radical generator) is preferably not lower than 100° C. nor higher than 800° C., and more preferably not lower than 200° C. nor higher than 600° C. A contact time of HCFO (1) and the radical generator in the reactor (reaction time) is preferably not less than 0.01 seconds not more than 1000 seconds, and more preferably not less than 0.05 seconds nor more than 100 seconds. Note that the contact time corresponds to the residence time of HCFO (1) and the radical generator in the reactor and can be controlled by adjusting the supply amounts (flow rates) of HCFO (1) and the radical generator to the reactor.

In the case where the radical generator is activated by light, the radical generator is irradiated with light. Specific examples of the irradiating light include an ultraviolet ray and a visible ray including light with a wavelength of not less than 200 nm nor more than 400 nm. Examples of a light source capable of such light irradiation in the isomerization reaction expressed by the aforesaid formula (3) include a high-pressure mercury lamp, a low-pressure mercury lamp, and a metal halide lamp.

A method of the light irradiation is not limited as long as it is a method capable of sufficiently activating the radical activator present in the reaction system throughout the reaction time, but in the case where, for example, HCFO (1) and the radical activator are mixed in advance to be supplied to the reactor, the method is, for example, a method in which a light source wearing a jacket that transmits at least light with the aforesaid wavelength necessary for the isomerization reaction, that is inert to the components present in the reaction system (HCFO (1), HCFO (2), the radical generator, and so on), and that is made of a corrosion resistant material is inserted into a gas of these components and the light is radiated to the components from the inside of the components. In a case where the light source generates heat, the aforesaid jacket is preferably a jacket having a cooling means, depending on the reaction temperature.

(Isomerization by Heat)

In the case where the aforesaid isomerization reaction is caused by the method of heating HCFO (1), HCFO (1) can undergo the aforesaid isomerization reaction by being heated in the reactor. Specifically, for example, HCFO (1) can undergo the isomerization reaction by being supplied into the reactor heated by a heating furnace such as an electric furnace. A reaction pressure at this time is preferably a normal pressure or a minute pressure of 0.2 MPa or less as in the case where the metal catalyst is used. Too low a reaction temperature makes the formation of the equilibrium of the aforesaid isomerization difficult, leading to a decrease in the conversion rate of HCFO (1) to HCFO (2). On the other hand, too high a reaction temperature causes the production of by-products due to, for example, the decomposition of HCFO (1), leading to a decrease in the conversion rate to HCFO (2). Accordingly, the heating temperature (reaction temperature) is preferably not lower than 400° C. nor higher than 1000° C., and more preferably not lower than 500° C. nor higher than 900° C. The residence time (reaction time) of HCFO (1) in the reactor is preferably not less than 0.001 seconds nor more than 1000 seconds, and more preferably not less than 0.01 seconds nor more than 100 seconds. By increasing the reaction temperature within the aforesaid preferable range or by increasing the reaction time within the aforesaid preferable range, it is possible to improve the conversion rate to HCFO (2).

(Outlet Gas)

In the method of producing HCFO of the present invention, HCFO (2) being the target substance can be obtained as an outlet gas of the aforesaid reactor. The outlet gas sometimes contains by-products produced from the impurities and the like contained in the raw material composition or produced as a result of the decomposition of HCFO (1) or the like. These by-products in the outlet gas can be removed by a known means such as distillation to a desired degree.

Further, in the aforesaid isomerization reaction, the equilibrium state of the isomerization is formed under the condition where the isomerization is caused as described above, and accordingly, even if the reaction condition (isomerization condition) is suitably adjusted, the outlet gas contains HCFO (1) being the starting substance in addition to HCFO (2) being the target substance.

HCFO (1) and HCFO (2) in the outlet gas are different in boiling point, with the boiling point of HCFO (1) (E-isomer) being 17° C. and the boiling point of HCFO (2) (Z-isomer) being 15° C. in the case where, for example, HCFO (1) is HCFO-1224yd (E), and thus can be separated by a usual distillation method. Therefore, the outlet gas obtained in the above is acid-cleaned or alkali-cleaned as required, is dehydrated with an adsorbent such as synthetic zeolite, is got rid of the by-products, and is distilled, whereby high-purity HCFO (2) and HCFO (1) can be obtained. Specifically, by supplying the outlet gas containing HCFO (1) and HCFO (2), which has undergone the above cleaning and so on, to a distillation column to distill the outlet gas, it is possible to obtain a distillate mainly composed of HCFO (2) from a column top and a bottom product containing HCFO (1) from a column bottom.

Out of the distillate and the bottom product thus obtained as a result of the distillation, the bottom product has larger HCFO (1)/HCFO (2) than the equilibrium ratio since the purity of HCFO (1) therein is increased. Therefore, by further subjecting the bottom product as the raw material composition to the condition where it is isomerized in the method of producing HCFO of the present invention, it is possible to convert HCFO (1) in the bottom product to HCFO (2).

Further, in a case where HCFO (1)/HCFO (2) in the distillate obtained as a result of the distillation is smaller than the equilibrium ratio, by subjecting the distillate as the raw material composition to the condition where it is isomerized in the method of producing HCFO of the present invention, it is possible to convert HCFO (2) in the distillate to HCFO (1). By thus repeating the isomerization reaction, the distillation separation of HCFO (1) and HCFO (2) obtained as a result of the isomerization reaction, and the re-isomerization of HCFO (1) obtained as a result of the distillation separation, it is possible to efficiently obtain HCFO (1) from HCFO (2).

In the case where HCFO (1) is obtained from HCFO (2), the conditions such as HCFO (1)/HCFO (2) in the raw material composition, the reaction temperature, and the reaction time are adjusted to the isomerization condition (2), in the aforesaid method of obtaining HCFO (2) from HCFO (1), specifically, the method using the metal catalyst, the method using the radical generator, or the method using the heating. In particular, by making HCFO (1)/HCFO (2) in the raw material composition smaller than the equilibrium ratio in the equilibrium reaction of the isomerization, it is possible to convert HCFO (2) to HCFO (1), as described above.

According to the method of producing HCFO of the present invention described above, it is possible to produce HCFO (2) (Z-isomer) by isomerizing HCFO (1) (E-isomer) by an industrially advantageous and efficient method. Further, by making HCFO (1)/HCFO (2) in the raw material composition smaller than the equilibrium ratio, it is possible to produce HCFO (1) (E-isomer) by isomerizing HCFO (2) (Z-isomer) by an industrially advantageous and efficient method.

(Working Medium for Heat Cycle)

A working medium for heat cycle of the present invention contains HCFO-1224yd (Z) obtained as a result of isomerizing HCFO-1224yd (E) whose X in the aforesaid formula (1) is the F atom by the above-described method of producing HCFO. The content of HCFO-1224yd (Z) to 100% by mass of the working medium for heat cycle is preferably 10% by mass or more, more preferably not less than 20% by mass nor more than 100% by mass, still more preferably not less than 40% by mass nor more than 100% by mass, yet more preferably not less than 60% by mass nor more than 100% by mass, and most preferably not less than 90% by mass nor more than 100% by mass.

In addition to HCFO-1224yd (Z), the working medium for heat cycle of the present invention may contain optional components, other than HCFO-1224yd (Z), usually contained in a working medium for heat cycle. Examples of the optional components include: hydrofluorocarbon (HFC) such as HFC-32, difluoroethane, trifluoroethane, tetrafluoroethane, HFC-125, pentafluoropropane, hexafluoropropane, heptafluoropropane, pentafluorobutane, and heptafluorocyclopentane; hydrofluoroolefin (HFO) such as HFO-1234yf, 1,2-difluoroethylene (HFO-1132), 2-fluoropropene (HFO-1261yf), 1,1,2-trifluoropropene (HFO-1243yc), 1,2,3,3,3-pentafluoropropene (HFO-1225ye), 1,3,3,3-tetrafluoropropene (HFO-1234ze), 3,3,3-trifluoropropene (HFO-1243zf), and 1,1,1,4,4,4-hexafluoro-2-butene (HFO-1336mzz); HCFO except HCFO-1224yd (Z), such as 1-chloro-2,2-difluoroethylene (HCFO-1122), 1,2-dichlorofluoroethylene (HCFO-1121), 1-chloro-2-fluoroethylene (HCFO-1131), 2-chloro-3,3,3-trifluoropropene (HCFO-1233xf), 1-chloro-3,3,3-tetrafluoropropene (HCFO-1233zd), and HCFO-1224yd (E); carbon dioxide, and hydrocarbon.

The working medium for heat cycle of the present invention is mixed with stabilizers such as an oxidation resistance improver, a heat resistance improver, and a metal deactivator, and in addition, with refrigeration oil such as mineral oil-based refrigeration oil such as naphthenic refrigeration oil or paraffinic refrigeration oil, or such as synthetic refrigeration oil such as ester refrigeration oil, ether refrigeration oil, polyglycol-based refrigeration oil, or hydrocarbon refrigeration oil, and is usable as a composition for heat cycle system in a heat cycle system.

As the heat cycle system in which the working medium for heat cycle of the present invention is used, a heat cycle system using a heat exchanger such as a condenser or an evaporator is used without any limitation. The heat cycle system, for example, a refrigeration cycle includes a mechanism which compresses a gaseous working medium by a compressor and cools it in a condenser to produce a high-pressure liquid, decreases the pressure by an expansion valve, and vaporizes the liquid by an evaporator at a low temperature to deprive it of heat by heat of vaporization.

As the heat cycle system, a refrigerating apparatus, an air-conditioning apparatus, a power generating system, a heat transport apparatus, a secondary cooling machine, or the like can be adopted without any limitation. As the heat cycle system in which the working medium for heat cycle of the present invention is used, a centrifugal freezer which is one kind of the aforesaid air-conditioning apparatus is preferable. As the centrifugal freezer, a low-pressure centrifugal freezer is preferable out of a low-pressure type and a high-pressure type. Note that the low-pressure type refers to, for example, a centrifugal freezer using a working medium to which the High Pressure Gas Safety Act is not applied, that is, a working medium not falling under the category of "liquefied gas, the pressure of which is not less than 0.2 MPa at its normal operating temperature and the pressure of which is currently not less than 0.2 MPa, or liquefied gas, the temperature of which is 35° C. or lower in the case where its pressure is 0.2 MPa or more".

HCFO-1224yd (Z) has a carbon-carbon double bond in its molecule and thus is low in global warming potential. Further, a ratio of halogen which reduces combustibility is high in its molecule. Therefore, the working medium for heat cycle of the present invention can be a working medium for heat cycle whose combustibility is reduced, whose influence on global warming is small, and which achieves excellent cycle performance. In particular, by using it in a centrifugal freezer in which a large amount of the working medium for heat cycle is filled, it is possible to obtain a heat cycle system having a small influence on global warming, has high safety, and achieves excellent cycle performance.

(Method of Producing HFO-1234yf)

A method of producing HFO-1234yf of the present invention includes: the step of obtaining HCFO-1224yd (Z) by isomerizing HCFO-1224yd (E) whose X in the aforesaid formula (1) is the F atom, by the above-described method of producing HCFO; and the step of obtaining HFO-1234yf by reducing HCFO-1224yd (Z) obtained in the step of obtaining HCFO-1224yd (Z) through its reaction with hydrogen. In this hydrogen reduction reaction, HCFO-1224yd (Z) and the hydrogen undergo the reaction expressed by the following formula (4), whereby HFO-1234yf is produced.

$$CF_3CF=CHCl+H_2 \rightarrow CF_3CF=CH_2+HCl \qquad (4)$$

In the method of producing HFO-1234yf of the present invention, HCFO-1224yd (Z) preferably undergoes the hydrogen reduction reaction in a vapor phase in the presence of a palladium catalyst carried by activated carbon. It is possible to cause the aforesaid hydrogen reduction reaction by filling the palladium catalyst carried by the activated carbon into a reactor formed of a material such as, for example, glass, iron, nickel, or an alloy mainly composed of any of these, to form a catalyst layer in the reactor, and supplying HCFO-1224yd (Z) and the hydrogen to the catalyst layer.

The palladium catalyst is not limited to a palladium simple substance but may be a palladium alloy. Further, the palladium catalyst may be a mixture of palladium and another metal, or may be a composite catalyst in which the palladium and the other metal are carried by carriers separately. In the case where the palladium catalyst is a palladium alloy, examples of the palladium catalyst include a palladium/platinum alloy catalyst and a palladium/rhodium alloy catalyst.

Examples of the activated carbon include those prepared using wood, charcoal, fruit shell, palm shell, peat, lignite, coal, or the like as a raw material, and one obtained from a plant raw material is more preferable than one obtained from a mineral raw material, and palm shell activated carbon is especially preferable. Examples of the shape of the activated carbon include coal briquette having a length of about not less than 2 mm nor more than 5 mm, crushed coal with about not less than 4 mesh nor more than 50 mesh, and granular coal. Among them, the crushed coal with not less than 4 mesh nor more than 20 mesh or the coal briquette is preferable.

The filling density of the palladium-carrying activated carbon in the catalyst layer is preferably not less than 0.5 g/cm³ nor more than 1 g/cm³, and more preferably not less than 0.6 g/cm³ nor more than 0.8 g/cm³. A ratio of HCFO-1224yd (Z) and the hydrogen which are introduced to the catalyst layer is preferably 0.7 or less in terms of a ratio of the number of moles of the chlorine atom in HCFO-1224yd (Z) and the number of moles of the hydrogen ($H_2$/Cl). In view of reducing the by-production of HFC-254eb, $H_2$/Cl is preferably 0.6 or less, and more preferably 0.5 or less. Further, in view of the yield of HFO-1234yf, $H_2$/Cl is preferably 0.1 or more, and more preferably 0.2 or more.

The temperature of the catalyst layer in the vapor phase reaction is preferably 50° C. or higher, more preferably 60° C. or higher, and especially preferably 80° C. or higher in view of reactivity. A reaction pressure is preferably a normal pressure in view of handleability.

According to the method of producing HFO-1234yf of the present invention, it is possible to efficiently produce HFO-1234yf while reducing the production of the by-products.

EXAMPLES

Next, examples will be described, but the present invention is not limited to these. Examples 1 to 20 and examples 24 and 25 are Examples, and examples 21 to 23 are Reference Examples.

Catalyst Preparation Example 1

An 81.5 mL chromium-magnesium composite oxide catalyst ($Cr_2O_3$: 98% by mass, MgO: 2% by mass, AG-23, Sakai Chemical) was filled into a tube-type reactor of stainless steel (SUS316) with a 23.4 mm inside diameter and a 400 mm height including an electric furnace, and the temperature was increased up to 200° C. while a nitrogen ($N_2$) gas was made to flow therein. While the temperature was maintained until no flow of water out of an outlet of the reactor was seen, the catalyst was dried. After the drying of the catalyst was finished, HCFC-22 was made to flow together with the $N_2$ gas to the reactor, and when a hot spot due to the activation of the filled catalyst reached an outlet end of the reactor, the temperature of the reactor was increased to 250° C., and while this state was kept for eight hours, the catalyst was subjected to activation treatment, whereby a catalyst 1 was obtained.

Catalyst Preparation Example 2

A catalyst 2 was obtained by the same preparation as in the catalyst preparation example 1 except that an alumina catalyst (N612N, JGC C & C) instead of the chromium-magnesium composite oxide catalyst was filled into the reactor.

Catalyst Preparation Example 3

A catalyst 3 was obtained by the same preparation as in the catalyst preparation example 1 except that an aluminum fluoride catalyst (Reagent Cica Extra Pure Grade: Kanto Kagaku) instead of the chromium-magnesium composite oxide catalyst was filled into the reactor.

Catalyst Preparation Example 4

A catalyst 4 was obtained by the same preparation as in the catalyst preparation example 1 except that a zirconium-zinc composite oxide catalyst ($ZrO_2$: 95% by mass, ZnC: 5% by mass, N.E CHEMCAT) instead of the chromium-magnesium composite oxide catalyst was filled into the reactor.

Catalyst Preparation Example 5

A catalyst 5 was obtained by the same preparation as in the catalyst preparation example 1 except that a catalyst in which 0.5% palladium was carried by carbon (a ratio of the palladium to the total amount of the catalyst is 0.5% by mass, manufactured by N.E. CHEMCAT, 0.5% Pd/C) instead of the chromium-magnesium composite oxide catalyst was filled into the reactor.

Catalyst Preparation Example 6

A 25% by mass aqueous iron (II) chloride solution was prepared, 200 mL columnar activated carbon (manufactured by Japan Enviro Chemicals, Ltd., current Osaka Gas Chemicals Co., Ltd., granular SHIRASAGI G2X) was immersed therein, and this state was kept for three hours. The filtered activated carbon was dried at 90° C. under a reduced pressure, whereby an iron (II) chloride-carrying activated carbon was obtained. An 81.5 mL of the iron (II) chloride-carrying activated carbon obtained above was filled into a tube-type reactor of stainless steel (SUS316) with a 23.4 mm inside diameter and a 400 mm height including an electric furnace, and the temperature was increased up to 200° C. while a nitrogen (N$_2$) gas was made to flow therein. While the temperature was maintained until no flow of water out of an outlet of the reactor was seen, the catalyst was dried. After the drying of the catalyst was finished, HCFC-22 was made to flow together with the N$_2$ gas to the reactor, and when a hot spot due to the activation of the filled catalyst reached an outlet end of the reactor, the temperature of the reactor was increased to 250° C., and while this state was kept for eight hours, the catalyst was subjected to activation treatment, whereby a catalyst 6 was obtained.

Catalyst Preparation Example 7

A catalyst 7 was obtained by the same preparation as in the catalyst preparation example 6 except that a 17% by mass aqueous nickel (II) chloride solution was used instead of the 25% by mass aqueous iron (II) chloride solution.

Catalyst Preparation Example 8

A catalyst 8 was obtained by the same preparation as in the catalyst preparation example 6 except that a 25% by mass aqueous copper (II) chloride solution was used instead of the 25% by mass aqueous iron (II) chloride solution.

Synthesis Example 1

Production of HCFO-1224yd

HCFO-1224yd was produced by the same method as the method described in WO 2011/162338 A1. Palladium-carrying activated carbon in which palladium was carried by activated carbon was filled into a tube-type reactor of stainless steel (SUS316) to form a catalyst layer. Thereafter, while the reactor was kept at 80° C. by a heating furnace, a mixed gas of CFO-1214ya and hydrogen which were mixed at a ratio of hydrogen (H$_2$)/CFO-1214ya=1/1 in terms of a molar ratio was supplied into the reactor. At this time, the mixed gas of CFO-1214ya and the hydrogen was supplied into the reactor such that the residence time of the mixed gas in the catalyst layer became 25 seconds.

After an outlet gas obtained from the aforesaid reactor was made to flow to an aqueous potassium hydroxide (KOH) solution with a concentration of 10% by mass and was got rid of an acid component, the outlet gas was made to flow to a dehydration column in which synthetic zeolite (Molecular sieve 4A) was filled, to be dehydrated. The dehydrated outlet gas was collected in a cylinder cooled by dry ice. The collected outlet gas was supplied as a sample to a column bottom of a distillation column whose theoretical number of stages was about 30, and was distilled by batch distillation at a 0.02 MPa operating pressure (gauge pressure), whereby a distillate containing 79.1% HCFO-1224yd (Z) and 19.3% HCFO-1224yd (E) (hereinafter, this distillate will be referred to as the "raw material composition A") was obtained from a column top of the distillation column.

Example 1

An 81.5 mL of the catalyst 1 was filled into a tube-type reactor of stainless steel (SUS316) with a 23.4 mm inside diameter and a 400 mm height (hereinafter also referred to as the reactor). The raw material composition A and a nitrogen gas (N$_2$) as a diluent gas were mixed at 27.9 NmL/min and 55.7 NmL/min respectively, and the mixture was pre-heated to 50° C. by a heating furnace. Thereafter, the pre-heated mixed gas of the raw material composition A and the nitrogen gas was made to flow to the reactor kept at 50° C. by the heating furnace, under a substantially atmospheric pressure. When an outlet gas from the reactor was collected and analyzed by GC (gas chromatography), the outlet gas had a composition of 88.2 (GC area %) HCFO-1224yd (Z) and 11.1% (GC area %) HCFO-1224yd (E) in terms of area percentage measured by GC (GC area %). Further, a reaction time (residence time of the raw material composition A in the reactor) was 49.5 seconds.

Examples 2 to 7

The same operations as that in the example 1 were conducted except that the temperature in the reactor (also referred to as the reaction temperature), the flow rate of the nitrogen gas (also referred to as the nitrogen flow rate), and the flow rate of the raw material composition A (also referred to as the raw material flow rate) were changed to the conditions in Table 1. Outlet gases of the reactor were collected and analyzed by GC. Table 1 shows the results of the GC analysis.

Examples 8 to 12

The same operations as that in the example 1 were conducted except that the metal catalyst was changed to the catalyst 2, and the reaction temperature, the nitrogen flow rate, and the raw material flow rate were changed to the conditions in Table 1. Outlet gases of the reactor were collected and analyzed by GC. Table 1 shows the results of the GC analysis.

TABLE 1

| | Reaction condition | | | | | Outlet gas composition | | | |
|---|---|---|---|---|---|---|---|---|---|
| Example | Reaction temperature [° C.] | Metal catalyst | Nitrogen flow rate [NmL/min] | Raw material flow rate [NmL/min] | Reaction time [second] | HCFO-1224 yd (Z) [GC area %] | HCFO-1224 yd (E) [GC area %] | Other [GC area %] | HCFO-1224 yd (E)/ HCFO-1224 yd (Z) [GC area % ratio] |
| Raw material | | Raw material composition A | | | | 79.1 | 19.3 | 1.6 | 0.244 |
| 1 | 50 | Catalyst 1 | 55.7 | 27.9 | 49.5 | 88.2 | 11.1 | 0.7 | 0.126 |
| 2 | 100 | Catalyst 1 | 48.3 | 24.1 | 49.5 | 89.5 | 9.3 | 1.2 | 0.104 |

TABLE 1-continued

| | Reaction condition | | | | | Outlet gas composition | | | |
|---|---|---|---|---|---|---|---|---|---|
| Example | Reaction temperature [° C.] | Metal catalyst | Nitrogen flow rate [NmL/min] | Raw material flow rate [NmL/min] | Reaction time [second] | HCFO-1224 yd (Z) [GC area %] | HCFO-1224 yd (E) [GC area %] | Other [GC area %] | HCFO-1224 yd (E)/ HCFO-1224 yd (Z) [GC area % ratio] |
| 3 | 150 | Catalyst 1 | 42.6 | 21.3 | 49.5 | 93.8 | 1.8 | 4.4 | 0.019 |
| 4 | 150 | Catalyst 1 | 85.1 | 42.6 | 24.7 | 95.6 | 3.4 | 1.1 | 0.035 |
| 5 | 150 | Catalyst 1 | 212.8 | 42.6 | 12.4 | 93.0 | 5.6 | 1.4 | 0.060 |
| 6 | 200 | Catalyst 1 | 38.1 | 19.0 | 49.5 | 94.5 | 3.2 | 2.3 | 0.033 |
| 7 | 200 | Catalyst 1 | 76.1 | 38.1 | 24.7 | 95.2 | 3.3 | 1.5 | 0.035 |
| 8 | 100 | Catalyst 2 | 48.3 | 24.1 | 49.5 | 93.9 | 4.9 | 1.3 | 0.052 |
| 9 | 150 | Catalyst 2 | 42.6 | 21.3 | 49.4 | 97.7 | 1.8 | 0.5 | 0.018 |
| 10 | 200 | Catalyst 2 | 76.1 | 38.1 | 24.7 | 96.4 | 2.8 | 0.8 | 0.029 |
| 11 | 200 | Catalyst 2 | 172.1 | 34.4 | 13.7 | 96.0 | 3.0 | 0.9 | 0.032 |
| 12 | 250 | Catalyst 2 | 172.1 | 34.4 | 12.4 | 90.3 | 5.0 | 4.7 | 0.055 |

Examples 13 to 18

81.5 mL of each of the catalysts 3 to 8 was filled into a tube-type reactor similar to that in the example 1 as shown in Table 2. The raw material composition A and a nitrogen gas ($N_2$) were mixed at a ratio of 19.0 NmL/min and 38.1 NmL/mn, and the mixture was pre-heated to 50° C. While the reactor was kept at 200° C. by a heating furnace, the pre-heated mixed gas of the raw material composition A and the nitrogen gas was made to flow to the reactor under a substantially atmospheric pressure. After each outlet gas obtained immediately after flowing in the reactor was made to flow to an aqueous potassium hydroxide (KOH) solution with a concentration of 10% by mass and was got rid of an acid component (acid cleaning), the outlet gas was made to flow to a dehydration column in which synthetic zeolite (Molecular sieve 4A) was filled, to be dehydrated. The dehydrated outlet gas was collected in a cylinder cooled by dry ice. The collected outlet gas was preparatively separated and its composition was analyzed by GC. Table 2 shows the results of the GC analysis.

046250. Specifically, HCFC-233da was dropped to a heated aqueous potassium hydroxide solution to undergo a reaction. A reaction solution obtained after the reaction was separated into an aqueous phase and an oil phase, whereby a 7194 g reaction crude solution as the oil phase containing 90.3% HCFO-1223xd (Z) and 5.7% HCFO-1223xd (E) was obtained. The obtained reaction crude solution was refined by distillation, whereby a 54 g bottom product containing 17.1% HCFO-1223xd (Z) and 79.6% HCFO-1223xd (E) (hereinafter, this bottom product will also be referred to as the "raw material composition B") and a 3597 g distillate containing 99.8% HCFO-1223xd (Z) and 0.2% HCFO-1223xd (E) (hereinafter, this distillate will be also referred to as the "raw material composition C") were obtained.

Examples 19, 20

The same operations as that in the example 1 were conducted except that, in the example 1, the raw material

TABLE 2

| | Reaction condition | | | | | Outlet gas composition | | | |
|---|---|---|---|---|---|---|---|---|---|
| Example | Reaction temperature [° C.] | Metal catalyst | Nitrogen flow rate [NmL/min] | Raw material flow rate [NmL/min] | Reaction time [second] | HCFO-1224 yd (Z) [GC area %] | HCFO-1224 yd (E) [GC area %] | Other [GC area %] | HCFO-1224 yd (E)/ HCFO-1224 yd (Z) [GC area % ratio] |
| Raw material | | Raw material composition A | | | | 79.1 | 19.3 | 1.6 | 0.244 |
| 13 | 200 | Catalyst 3 | 38.1 | 19.0 | 49.5 | 94.0 | 4.6 | 1.4 | 0.049 |
| 14 | 200 | Catalyst 4 | 38.1 | 19.0 | 49.5 | 93.8 | 4.2 | 2.0 | 0.045 |
| 15 | 200 | Catalyst 5 | 38.1 | 19.0 | 49.5 | 95.6 | 3.4 | 1.0 | 0.036 |
| 16 | 200 | Catalyst 6 | 38.1 | 19.0 | 49.5 | 94.7 | 3.1 | 2.2 | 0.033 |
| 17 | 200 | Catalyst 7 | 38.1 | 19.0 | 49.5 | 92.9 | 4.6 | 2.5 | 0.050 |
| 18 | 200 | Catalyst 8 | 38.1 | 19.0 | 49.5 | 89.5 | 9.6 | 0.9 | 0.107 |

As shown in Tables 1, 2, it is seen that it is possible to convert HCFO-1224yd (E) to HCFO-1224yd (Z) with a very high yield (conversion rate).

Synthesis Example 2

Synthesis of HCFO-1223xd

HCFO-1223xd was produced by the same method as the method described in International Publication No. 2014/ composition B was used instead of the raw material composition A, and the reaction temperature, the nitrogen flow rate, and the raw material flow rate were changed to those in Table 3. Outlet gases of the reactor were collected, and compositions of the collected outlet gases were analyzed by GC, as in the example 1. Table 3 shows the results of the GC analysis.

TABLE 3

| Example | Reaction condition ||||| Outlet gas composition ||||
|---|---|---|---|---|---|---|---|---|---|
| | Reaction temperature [° C.] | Metal catalyst | Nitrogen flow rate [NmL/min] | Raw material flow rate [NmL/min] | Reaction time [second] | HCFO-1223 xd (Z) [GC area %] | HCFO-1223 xd (E) [GC area %] | Other [GC area %] | HCFO-1223 xd (E)/ HCFO-1223 xd (Z) [GC area % ratio] |
| Raw material | Raw material composition B ||||| 17.1 | 79.6 | 3.3 | 4.660 |
| 19 | 250 | Catalyst 1 | 29.1 | 47.8 | 33.2 | 94.5 | 2.6 | 2.9 | 0.027 |
| 20 | 300 | Catalyst 1 | 29.1 | 23.9 | 44.0 | 91.4 | 3.4 | 5.2 | 0.037 |

As shown in Table 3, it is seen that it is possible to convert HCFO-1223xd (E) to HCFO-1223xd (Z) with a very high yield (conversion rate).

Examples 21 to 23

The same operations as that in the example 1 were conducted except that, in the example 1, the raw material composition C was used instead of the raw material composition A, and the reaction temperature, the nitrogen flow rate, and the raw material flow rate were changed to those in Table 4. Outlet gases of the reactor were collected, and compositions of the collected outlet gases were analyzed by GC, as in the example 1. Table 4 shows the results of the GC analysis.

TABLE 4

| Example | Reaction condition ||||| Outlet gas composition ||||
|---|---|---|---|---|---|---|---|---|---|
| | Reaction temperature [° C.] | Metal catalyst | Nitrogen flow rate [NmL/min] | Raw material flow rate [NmL/min] | Reaction time [second] | HCFO-1223 xd (Z) [GC area %] | HCFO-1223 xd (E) [GC area %] | Other [GC area %] | HCFO-1223 xd (E)/ HCFO-1223 xd (Z) [GC area % ratio] |
| Raw material | Raw material composition C ||||| 99.8 | 0.2 | 0.0 | 0.002 |
| 21 | 150 | Catalyst 1 | 35.9 | 8.64 | 70.87 | 97.5 | 1.2 | 1.2 | 0.013 |
| 22 | 200 | Catalyst 1 | 32.1 | 34.34 | 42.49 | 95.3 | 1.7 | 3.0 | 0.017 |
| 23 | 250 | Catalyst 1 | 32.1 | 28.61 | 42.06 | 93.9 | 3.0 | 3.2 | 0.032 |

As shown in Table 4, it is seen that, by making HCFO-1223xd (E)/HCFO-1223xd (Z) in the raw material composition smaller than the equilibrium ratio, it is possible to convert HCFO-1223xd (Z) to HCFO-1223xd (E).

Example 24

The same tube-type reactor as that in the example 1 (a tube-type reactor of SUS316 with a 23.4 mm inside diameter and a 400 mm height) was used, and the heating furnace was set to a temperature of 400° C. to heat the reactor. 442.6 NmL/min of the raw material composition A and 5.2 NmL/min chlorine as a radical generator were mixed at this ratio (molar ratio of HCFO-1224yd (E)/chlorine in the raw material composition A=85.1/1), and the mixture was pre-heated to 200° C., was supplied to the reactor heated to the aforesaid temperature, and was made to flow under a substantially atmospheric pressure. An outlet gas immediately after flowing in the reactor was made to flow to an aqueous KOH solution with a concentration of 10% by mass, was got rid of an acid component (acid cleaning), and thereafter was made to flow to a dehydration column in which synthetic zeolite (Molecular sieve 4A) was filled, to be dehydrated. The dehydrated outlet gas was collected in a cylinder cooled by dry ice. The collected outlet gas was preparatively separated and its composition was analyzed by GC. Table 5 shows the result of the GC analysis.

Example 25

The same operation as that in the example 24 was conducted except that, in the example 24, the kind of the radical generator was changed from chlorine to air (HCFO-1224yd (E)/air (volume ratio) in the raw material composition A=85.1/1). An outlet gas collected in the cylinder was preparatively separated, and its composition was analyzed by GC. Table 5 shows the result of the GC analysis.

TABLE 5

| | Reaction condition | | | | | Outlet gas composition | | | |
|---|---|---|---|---|---|---|---|---|---|
| | | Radical generator | | Nitrogen | Raw material | Reaction | HCFO- | HCFO- | | HCFO-1224 yd (E)/ |
| Example | Reaction temperature [° C.] | Kind | Flow rate [NmL/min] | flow rate [NmL/min] | flow rate [NmL/min] | time [second] | 1224 yd (Z) [GC area %] | 1224 yd (E) [GC area %] | Other [GC area %] | HCFO-1224 yd (Z) [GC area % ratio] |
| Raw material | | Raw material composition A | | | | | 79.1 | 19.3 | 1.6 | 0.244 |
| 24 | 400 | Chlorine | 5.2 | — | 442.6 | 4.4 | 87.6 | 10.5 | 1.9 | 0.120 |
| 25 | 400 | Air | 5.2 | — | 442.6 | 4.4 | 90.0 | 7.4 | 2.6 | 0.083 |

As shown in Table 5, it is seen that it is possible to convert HCFO-1224yd (E) to HCFO-1224yd (Z) with a very high yield (conversion rate).

What is claimed is:

1. A method for producing a hydrochlorofluoroolefin, the method comprising isomerizing a compound of formula (1) contained in a raw material composition, to obtain a compound of formula (2):

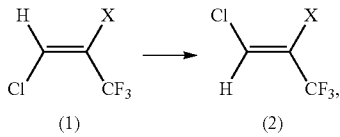

wherein:
X represents a fluorine atom; and
the isomerizing comprises contacting the compound of formula (1) with a metal catalyst at a contact temperature of not lower than 150° C. and not higher than 350° C.

2. The method of producing the hydrochlorofluoroolefin according to claim 1, wherein the metal catalyst is at least one selected from a group consisting of a metal simple substance, a metal oxide, and a metal halide.

3. The method of producing hydrochlorofluoroolefin according to claim 1, wherein the metal catalyst comprises at least one metal element selected from a group consisting of a group 4 metal element, a group 6 metal element, a group 8 metal element, a group 9 metal element, a group 10 metal element, a group 11 metal element, a group 12 metal element, and a group 13 metal element.

4. The method of producing the hydrochlorofluoroolefin according to claim 1, wherein the metal catalyst is a metal oxide.

5. The method of producing hydrochlorofluoroolefin according to claim 1, wherein the metal catalyst is at least one selected from a group consisting of aluminum oxide and chromium oxide.

6. The method of producing the hydrochlorofluoroolefin according to claim 1, wherein:

the raw material composition comprises the compound of formula (1) and the compound of formula (2); and
a molar ratio of the compound of formula (1) to the compound of formula (2) in the raw material composition is 5/95 or more.

7. The method of producing the hydrochlorofluoroolefin according to claim 1, wherein the isomerizing occurs in a vapor phase.

8. The method of producing the hydrochlorofluoroolefin according to claim 1, wherein the contact temperature of the compound of formula (1) and the metal catalyst ranges from 150° C. to 250° C.

9. The method of producing the hydrochlorofluoroolefin according to claim 1, wherein a contact time of the compound of formula (1) with the metal catalyst ranges from 0.1 seconds to 1000 seconds.

10. The method of producing the hydrochlorofluoroolefin according to claim 1, wherein, after the isomerizing, a product composition comprises the compound of formula (1) and the compound of formula (2).

11. The method of producing the hydrochlorofluoroolefin according to claim 10, wherein, before the isomerizing, the raw material composition comprises the compound of formula (2).

12. A method of producing 2,3,3,3-tetrafluoropropene, the method comprising hydrogen-reducing the compound of formula (2) obtained in the method of claim 1, to obtain the 2,3,3,3-tetrafluoropropene.

13. The method of producing the hydrochlorofluoroolefin according to claim 1, wherein the isomerizing comprises contacting the compound of formula (1) with a metal catalyst at a contact temperature of not lower than 150° C. and less than 250° C.

14. The method of producing the hydrochlorofluoroolefin according to claim 9, wherein the contact time ranges from 24.7 seconds to 1000 seconds.

15. The method of producing the hydrochlorofluoroolefin according to claim 1, wherein the metal catalyst comprises at least one metal element selected from a group consisting of a group 4 metal element, a group 6 metal element, a group 8 metal element, a group 9 metal element, a group 10 metal element, a group 12 metal element, and a group 13 metal element.

* * * * *